United States Patent
Carney

(10) Patent No.: US 7,854,740 B2
(45) Date of Patent: Dec. 21, 2010

(54) INTRALUMINAL GUIDANCE SYSTEM USING BIOELECTRIC IMPEDANCE

(75) Inventor: Alan Carney, Menlo (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 12/417,363

(22) Filed: Apr. 2, 2009

(65) Prior Publication Data

US 2009/0192405 A1 Jul. 30, 2009

Related U.S. Application Data

(62) Division of application No. 11/412,767, filed on Apr. 27, 2006, now abandoned.

(51) Int. Cl.
*A61B 17/22* (2006.01)

(52) U.S. Cl. .................. 606/159; 600/585; 600/373; 600/547

(58) Field of Classification Search .............. 600/547, 600/585, 373; 606/159
See application file for complete search history.

(56) References Cited

U.S. PATENT DOCUMENTS

| | | | |
|---|---|---|---|
| 5,443,470 A | | 8/1995 | Stern et al. |
| 6,080,149 A | * | 6/2000 | Huang et al. ............... 606/32 |
| 6,095,987 A | | 8/2000 | Shmulewitz et al. |
| 6,416,523 B1 | | 7/2002 | Lafontaine |
| 6,478,769 B1 | | 11/2002 | Parker |
| 6,496,725 B2 | | 12/2002 | Kamada et al. |
| 6,565,588 B1 | | 5/2003 | Clement et al. |
| 6,620,139 B1 | | 9/2003 | Plicchi et al. |
| 6,824,550 B1 | | 11/2004 | Noriega et al. |
| 6,962,587 B2 | | 11/2005 | Johnson et al. |
| 6,980,853 B2 | | 12/2005 | Miyoshi et al. |
| 2001/0012934 A1 | * | 8/2001 | Chandrasekaran et al. .... 606/41 |
| 2002/0016624 A1 | | 2/2002 | Patterson et al. |
| 2002/0046756 A1 | | 4/2002 | Laizzo et al. |
| 2002/0072740 A1 | * | 6/2002 | Chandrasekaran et al. .... 606/41 |

(Continued)

FOREIGN PATENT DOCUMENTS

EP 0882430 8/2002

(Continued)

OTHER PUBLICATIONS

Simulation of Electrode Impedance and Current Densities Near an Atherosclerotic Lesion, May 2-4,2002 IEEE-EMB Special Topic Conference, pp. 57-61.

(Continued)

*Primary Examiner*—Max Hindenburg
*Assistant Examiner*—Michael C Stout

(57) ABSTRACT

A system using bioelectric impedance to guide a flexible elongate transluminal device through an occlusion in a vessel. The device can be a guidewire or a device for performing an atherectomy, discectomy, ablation or similar technique. The device includes a first electrode disposed on a distal portion of the device. A second electrode is disposed in electric contact with the patient separate from the first electrode. An electric current is supplied between the first and second electrodes and a voltage drop is measured between the first and second electrodes. The voltage drop is converted to bioelectric impedance. Based on the impedance measurement, a clinician can determine if the device is approaching the vessel wall, permitting the clinician to redirect the device away from the vessel wall.

6 Claims, 4 Drawing Sheets

U.S. PATENT DOCUMENTS

| | | | |
|---|---|---|---|
| 2003/0109871 A1* | 6/2003 | Johnson et al. | 606/42 |
| 2003/0130711 A1* | 7/2003 | Pearson et al. | 607/101 |
| 2003/0139763 A1 | 7/2003 | Duerig et al. | |
| 2003/0163128 A1* | 8/2003 | Patil et al. | 606/41 |
| 2003/0195433 A1* | 10/2003 | Turovskiy et al. | 600/564 |
| 2004/0122421 A1* | 6/2004 | Wood | 606/41 |
| 2004/0167412 A1 | 8/2004 | Ohhashi et al. | |
| 2004/0220562 A1* | 11/2004 | Garabedian et al. | 606/41 |
| 2005/0096647 A1* | 5/2005 | Steinke et al. | 606/41 |
| 2006/0064038 A1 | 3/2006 | Omata et al. | |
| 2006/0085049 A1 | 4/2006 | Cory et al. | |
| 2006/0206106 A1* | 9/2006 | Scholl et al. | 606/32 |
| 2007/0062547 A1* | 3/2007 | Pappone | 128/898 |

FOREIGN PATENT DOCUMENTS

| WO | WO97/45157 | 12/1997 |
|---|---|---|
| WO | WO2004/071288 | 8/2004 |

OTHER PUBLICATIONS

Simulated Characterization of Atherosclerotic Lesions in the Coronary Arteries by Measurement of Bioimpedance, IEE Transactions on Biomedical Engineering, vol. 50, No. 7, Jul. 2003.

* cited by examiner

INTRALUMINAL GUIDANCE SYSTEM USING BIOELECTRIC IMPEDANCE

CROSS-REFERENCE TO RELATED APPLICATIONS

This is a division of U.S. patent application Ser. No. 11/412,767, filed Apr. 27, 2006.

FIELD OF THE INVENTION

The disclosure relates generally to a guidance system for use in a patient's vessel, and more particularly, to a system for guiding an intra-luminal device through an arterial chronic total occlusion (CTO) using bioelectric impedance.

BACKGROUND OF THE INVENTION

Stenotic lesions may comprise a hard, calcified substance and/or a softer thrombus material, each of which forms on the lumen walls of a blood vessel and restricts blood flow there through. Intra-luminal treatments, such as balloon angioplasty, stent deployment, atherectomy, and thrombectomy are well known and have proven effective in the treatment of such stenotic lesions. These treatments often involve the insertion of a therapy catheter into a patient's vasculature, which may be torturous and may have numerous stenoses of varying degrees throughout its length. In order to place the distal, treatment portion of a catheter within the treatment site, a steerable guidewire is typically introduced and tracked from an incision, through the vessels, and across the lesion. Then, a catheter, e.g., a balloon catheter, perhaps carrying a stent, can be tracked over the guidewire to the treatment site. Ordinarily, the distal end of the guidewire is quite flexible so that as it is directed, or steered through the lumen, it can find its way through the turns of the typically irregular passageway without perforating or otherwise damaging the vessel wall.

In some instances, the extent of occlusion of the lumen is so severe that the lumen is completely or nearly completely obstructed, leaving virtually no passageway for the guidewire. Such a condition may be described as a total occlusion. If this occlusion persists for a long period of time, the lesion is referred to as a chronic total occlusion or CTO. Furthermore, in the case of diseased blood vessels, the lining of the vessels may be characterized by the prevalence of atheromatous plaque, which may form total occlusions. The extensive plaque formation of a chronic total occlusion typically has a fibrous cap surrounding softer plaque material. This fibrous cap may present a surface that is difficult to penetrate with a conventional guidewire, and the typically flexible distal tip of the guidewire may be unable to cross the lesion.

Thus, for treatment of total occlusions, guidewire having stiffer distal tips have been employed to recanalize a total occlusion. However, blood vessels are not straight and fluoroscopic visualization of the natural path through an occlusion is poor because there is little or no flow of radiographic contrast through the occlusion. Therefore, simply using a stiffer guidewire to push through an occlusion increases the risk that the guidewire tip will penetrate the vessel wall.

Atherectomy is another established treatment for occlusions. Atherectomy procedures typically involve inserting a cutting or ablating device through the access artery, e.g. the femoral artery or the radial artery, and advancing it through the vascular system to the occluded region, and rotating the device at high speed via a drive shaft to cut through or ablate the plaque over the wire. The removed plaque or material can then be suctioned out of the vessel or be of such fine diameter that it is cleared by the reticuloendothelial system. Atherectomy devices also present the danger of unwanted perforation of a vessel wall by the material removal device. This can occur when the material removal device improperly engages the vessel wall, for example when the material removal device is not oriented substantially parallel to the axis of the vessel. In this situation, the material removal device, e.g. cutter or abrasive ablator, may improperly engage the vessel wall and cause unwanted damage thereto. Other ablation and discectomy devices also present the danger of damage to a vessel wall.

Thus, there is a need for a device and method to reduce the risk of damage to a vessel wall when a guidewire or a device for performing an atherectomy, discectomy, ablation or similar procedure is crossing an occlusion.

Electrical impedance is the opposition to the flow of an alternating current, which is the vector sum of ohmic resistance plus additional resistance, if any, due to induction, to capacitance, or to both. Bioelectric impedance is known, e.g., for use in measuring body fat composition. For example, bathroom scales may include means to measure body fat composition using bioelectric impedance. According to this technique, a person's body fat is measured by determining the impedance of the person's body to electrical signals, and calculating the percent body fat based upon the measured impedance and other variables, such as height, weight, age, and sex.

Bioelectric impedance is typically determined by supplying a harmless electric current through at least two separated electrodes that contact portions of a body, and measuring a voltage across the body portion. This voltage is measured either (1) via the same electrodes through which current is supplied, or (2) via one or more distinct pairs of voltage-measuring electrodes. The bioelectric impedance is then readily calculated from the current and the measured voltage. The calculated bioelectric impedance may be compared to an expected value or range of common or known values, or it may be compared to one or more bioelectric impedance values previously measured in, and calculated for the same patient.

BRIEF SUMMARY OF THE INVENTION

The present disclosure is a system that uses bioelectric impedance to guide an elongate intraluminal device through an occlusion in a vessel. The device can be a medical guidewire or a therapeutic catheter for performing an angioplasty, atherectomy, discectomy, ablation or similar procedure. The device includes an electrode disposed on a distal portion of the device. A second electrode is disposed separately of the first electrode, either on the same device or on a separate device. For example, the second electrode may be mounted on a skin electrode or on a balloon of a catheter. The system provides an electric power source and an impedance monitor for connection to the first and second electrodes.

During use of the above system to guide an elongate device through a vessel occlusion in a patient, a first electrode is disposed adjacent the occlusion targeted for crossing. A second electrode is spaced apart from the first electrode and disposed in electrical contact with the patient's tissue, e.g., against the wall of the occluded or another vessel. The second electrode may be a skin electrode in contact with the patient's skin. As the elongate device is advanced through the occlusion, an electric current is supplied between the first and second electrodes and a voltage drop is measured between the first and second electrodes. The voltage drop is converted arithmetically to a calculated bioelectric impedance. By comparing the measured/calculated bioelectric impedance to a known, e.g., expected standard or previously measured impedance, a clinician can determine whether the device is approaching the vessel wall and posing a risk of perforating the wall. With this information, the clinician can halt advancement of the device, and possibly redirect the device away from the vessel wall.

BRIEF DESCRIPTION OF DRAWINGS

The foregoing and other features and advantages of the disclosure will be apparent from the following description of the disclosure as illustrated in the accompanying drawings. The accompanying drawings, which are incorporated herein and form a part of the specification, further serve to explain the principles of the disclosure and to enable a person skilled in the pertinent art to make and use the disclosure. The drawings are not to scale.

DETAILED DESCRIPTION OF THE INVENTION

Specific embodiments of the present disclosure are now described with reference to the figures, where like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
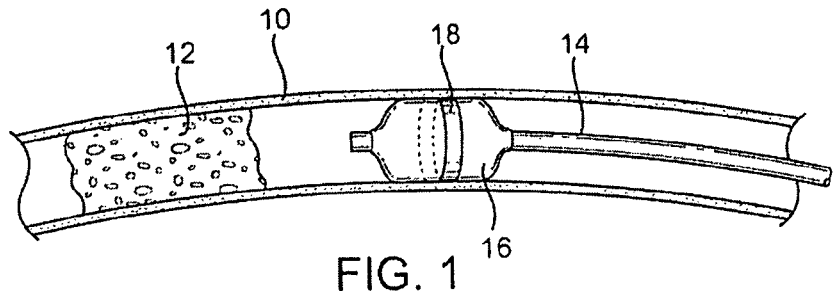
FIG. 1 is a partial cut-away view of a vessel including an occlusion and illustrating a system in accordance with an embodiment of the present disclosure.
Figure 2:
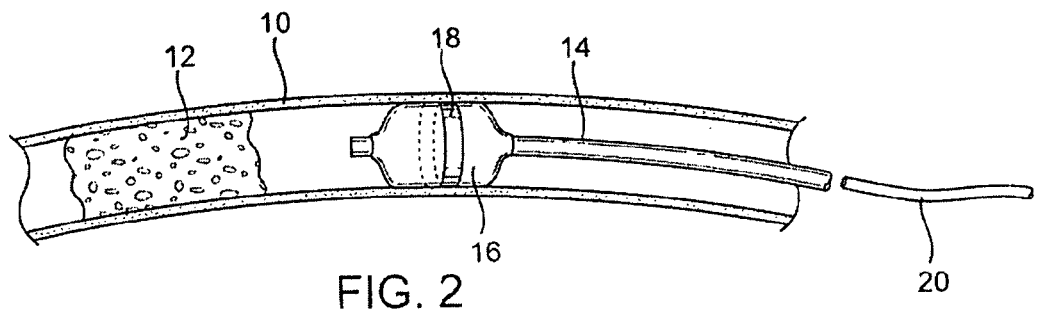
FIG. 2 illustrates the system as shown in FIG. 1, with the introduction of a microcatheter.
Figure 3:
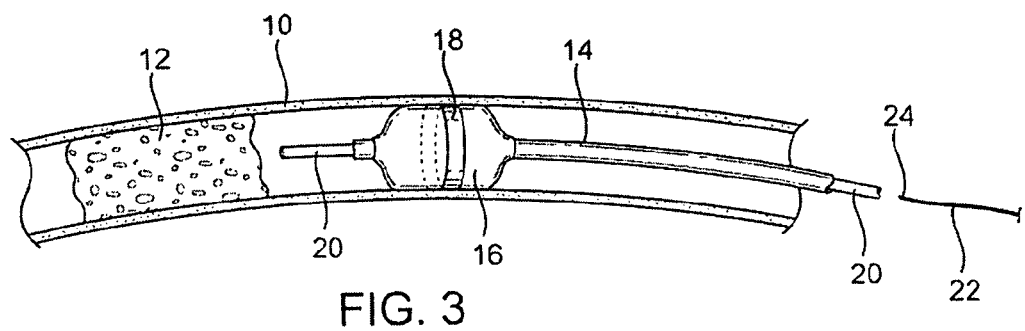
FIG. 3 illustrates the system as shown in FIG. 2, with the introduction of a guidewire.
Figure 4:
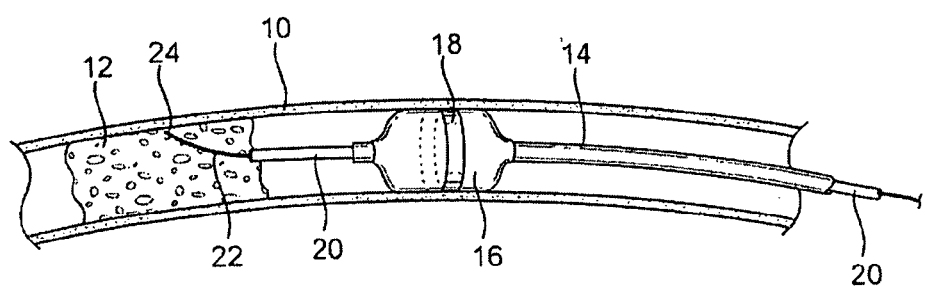
FIG. 4 illustrates the system as shown in FIG. 3, with the guidewire advanced into the occlusion.

The present disclosure is directed to a system and method for guiding an elongate medical device, such as a guidewire or catheter for performing an angioplasty, atherectomy, dissection, or ablation, through an occlusion in a patient's vessel. Although the present description relates to crossing an occlusion in a blood vessel, such as an arterial stenosis, the invention is not so limited, and may be applicable for providing guidance during crossing of other blockages in other passageways in a patient. A blood vessel 10 with an occlusion 12 blocking blood flow through it is shown in FIGS. 1-4. A balloon catheter 14 with a balloon 16 near its distal end is advanced through the vasculature to a position proximal to occlusion 12, as shown in FIG. 1. Catheter 14 and balloon 16 can be made of materials known to those skilled in the art. In an embodiment of the present disclosure, balloon 16 includes a second, ring electrode 18 disposed about its periphery. Optionally, a micro-catheter 20 is advanced through catheter 14 such that a distal portion of micro-catheter 20 extends from a distal end of catheter 14, as shown in FIGS. 2 and 3. A guidewire 22 may be advanced through balloon catheter 14 and optional micro-catheter 20 and extends into occlusion 12, as shown in FIGS. 3 and 4. Although FIG. 1 shows balloon 16 inflated for clarity of the illustration, balloon 16 is typically advanced through blood vessel 10 in an uninflated condition. Balloon 16 is inflated prior to advancing guidewire through occlusion 12. Thus, balloon 16 need not be inflated until after the step shown in FIG. 3, although it can be inflated at anytime after being advanced through blood vessel 10 to the position shown in FIG. 1. Further, although FIGS. 1-4 show balloon 16 with ring electrode 18, any suitable device can be equipped with an electrode, provided that the electrode can be maintained in electrical contact with the wall of the vessel during crossing of the occlusion. For example, a second guidewire could be used with an electrode disposed thereon and placed against the wall of the vessel. Alternatively, the second electrode may be positionable in electrical contact with the patient's tissue in a different vessel, or outside of the patient's vascular system, or outside the patient's body, viz. a skin electrode as will be discussed below with respect to electrode 50.

Figure 6:
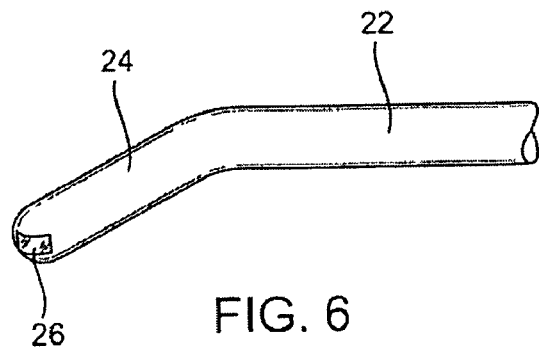
FIG. 6 is a side view of a steerable guidewire of the present disclosure.

Referring to FIG. 6, guidewire 22 includes a tip 24 with a first electrode 26 disposed thereon. Guidewire 22 in FIG. 6 is shown as a steerable guidewire. Any guidewire suitable for crossing an occlusion may be used, as would be apparent to those skilled in the art. Guidewire 22 can be fabricated from materials as known to those skilled in the art. Electrode 26 may be an electrically conducting electrode and can be fabricated from a variety of conductive materials known in the art, including stainless steel, copper, silver, gold, platinum and alloys and combinations thereof.

Figure 5:
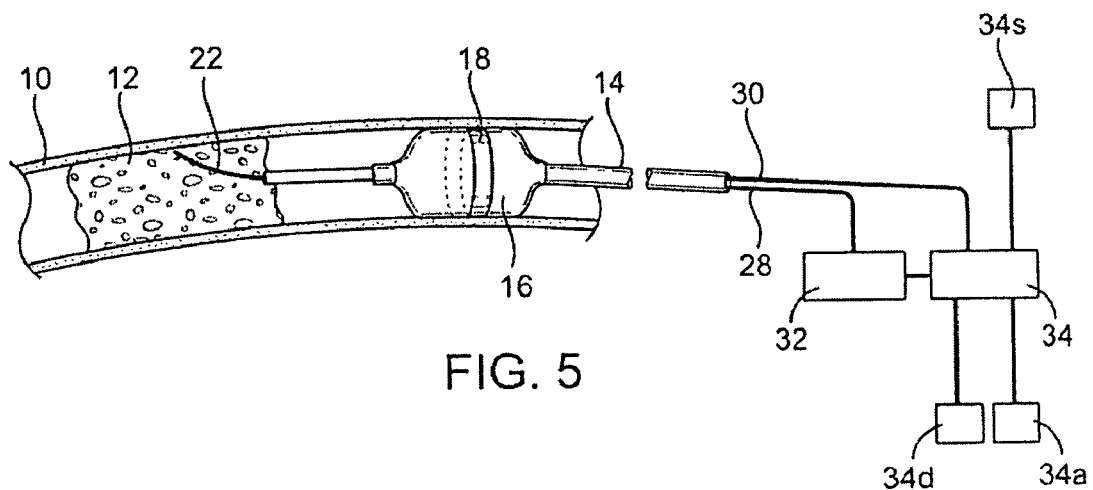
FIG. 5 is a partial cut-away view of the system of FIGS. 1-4 illustrating a schematic representation of equipment outside of the vessel.

Referring to FIG. 5, an electrically conductive lead 28 communicates with electrode 26, as by an insulated wire (not shown) within guidewire 22, and lead 28 extends outside of the body to an electric power source 32. An electrically conductive lead 30 communicates with ring electrode 18, as by an insulated or otherwise electrically isolated wire (not shown) within catheter 14, and lead 30 extends outside the body to an electrical impedance monitor 34. Power source 32 and impedance monitor 34 are connected together externally or they may be combined in an integral device. Power source 32 and impedance monitor 34, in conjunction with leads 28, 30 and electrodes 18, 26 form a complete electrical circuit that includes a portion of a patient's body extending between electrodes 18, 26. The materials that define the portion of a patient's body in the electrical circuit will be discussed in detail below.

Power source 32 generates a harmless electric current through lead 28 between electrodes 26 and 30. The current may be a pulsed and/or alternating current and the selected alternating frequency may be in the range of 1 kHz to 500 kHz or other suitable frequencies known to those of skill in the art of bioelectric impedance. Ring electrode 18 may be fabricated from a variety of conductive materials known in the art, including stainless steel, copper, silver, gold, platinum and alloys and combinations thereof. In an alternative embodiment of the disclosure, a smaller, viz., non-ring shaped electrode or a plurality of electrodes may be disposed on balloon 16, provided such that that the electrode(s) may be brought into electrical contact with the wall of vessel 10, as by inflating balloon 16 into apposition with the vessel wall.

In practice, as guidewire 22 is advanced through occlusion 12, power source 32 generates an electric current through leads 28, 30 and through the patient's tissue between electrodes 18, 26. The current can be pulsed in a suitable range of pulse frequencies as may be determined by those of skill in the art of bioelectric impedance. While current is flowing through electrodes 18, 26, a corresponding resistance or voltage drop is measured between electrodes 18, 26. The voltage drop is arithmetically converted to an impedance measurement at impedance monitor 34. Impedance monitor 34 may include logic resources, such as a microprocessor, and/or memory resources, such as a RAM or DRAM chip, configured to analyze, store and display bioelectric information derived from electrodes 18, 26. For example, impedance monitor 34 may include a voltage-current converting circuit, an amplifying circuit, an A/D converting circuit, and an impedance arithmetic operation section. Impedance monitor 34 may further include, or may be coupled to, a display device 34d, such as a cathode ray tube, liquid crystal display, plasma display, flat panel display or the like.

Occlusions 14 are generally made of atherosclerotic plaques. Although atherosclerotic plaques may vary, they contain many cells; mostly these are derived from cells of the wall that have divided wildly and have grown into the surface layer of the blood vessel, creating a mass lesion. Plaques also contain cholesterol and cholesterol esters, commonly referred to as fat, that lie freely in the space between the cells and within the cells themselves. A large amount of collagen is present in the plaques, particularly in advanced plaques of the type which cause clinical problems. Additionally, human plaques contain calcium to varying degrees, hemorrhagic material including clot and grumous material composed of dead cells, fat and other debris. Plaques also contain about 10-20% water. This general composition of atherosclerotic plaques results in a relatively high electrical resistance (and correspondingly high bioelectric impedance), as compared to more lean body tissue, such as vessel wall 10.

Thus, when electrode 26 located on tip 24 of guidewire 22 is disposed generally at the center of occlusion 12, the electric current from power source 32 passes through the relatively high resistance atherosclerotic plaque of occlusion 12 before reaching the relatively lower resistance wall of vessel 10. The current then travels through the wall of vessel 10 to ring electrode 18. If tip 24 of guidewire 22 goes off-course such that it becomes closer to the wall of vessel 10, then the current travels a shorter distance through less thickness of the relatively high resistance atherosclerotic plaque of occlusion 12 before reaching the wall of vessel 10. Ultimately, if tip 24 approaches the wall of vessel 10, the current passes through very little of the relatively high resistance atherosclerotic plaque of occlusion 12 before reaching vessel 10. Thus, the impedance detected between electrodes 18, 26 and displayed at impedance monitor 34 will decrease if tip 24 approaches the wall of vessel 10.

A clinician may stop the advancement of, and/or attempt to redirect guidewire 22 away from the wall of vessel 10 when the bioelectric impedance drops below a certain threshold value. Such a threshold value may be measured and calculated by measuring bioelectric impedance in undiseased vessel tissue adjacent target occlusion 12, using the system of the disclosure prior to advancing guidewire 22 into occlusion 12. Alternatively, a bioelectric impedance threshold value for comparison during crossing of occlusion 12 may be a value that may be predicted by an experienced clinician, or a value that a large number of similar patients are known to have in common, or a value that is otherwise available, e.g., from a printed or electronic reference source. The clinician's reaction to the bioelectric impedance reaching a low limit may prevent tip 24 of guidewire 22 from piercing vessel 10. Impedance monitor 34 may further include an alarm 34a such that when the impedance reaches a predetermined limit, the alarm is activated, thereby alerting the clinician that the impedance has reached the predetermined limit.

Figure 7:
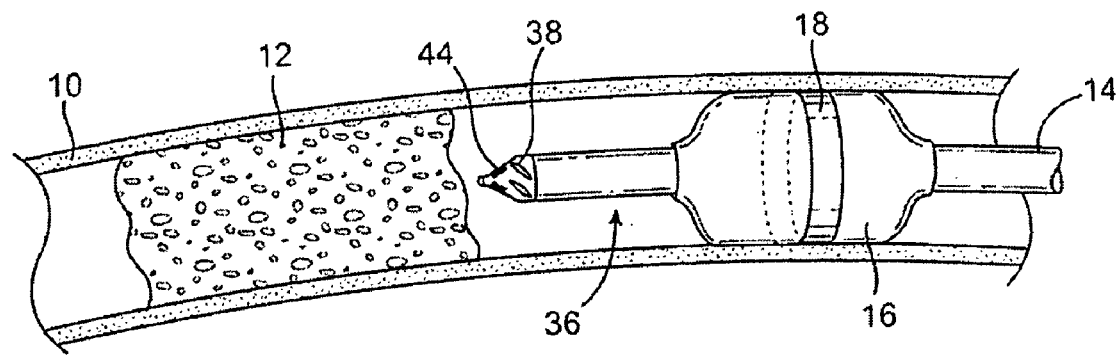
FIG. 7 is a partial cut-away view of a vessel including an occlusion and illustrating another embodiment in accordance with the present disclosure.

FIG. 7 shows another embodiment of the present disclosure which is similar to the embodiment shown in FIGS. 1-6 except that an atherectomy device 36 is advanced through balloon catheter 14 into occlusion 12. Atherectomy device 36 includes a cutting head 38 that is rotated at high speed, e.g., via a drive shaft to cut or ablate a passageway through the plaque of occlusion 12. The removed plaque or material may be suctioned out of the vessel as is known to those skilled in the art. A first electrode 44 is disposed on cutting head 38. An electric current is provided through electrodes 18, 44 and a voltage drop is measured between electrodes 18, 44, in the same manner as described above with respect to the embodiment of FIGS. 1-6 (the power source, impedance monitor, and leads are not shown). The measured voltage drop is converted to impedance by the impedance monitor. Based on the calculated impedance, it can be determined if cutting head 38 is too close to the wall of vessel 10. In such a case, advancement of atherectomy device 36 may be halted and/or cutting head 38 may be redirected away from the wall of vessel 10. In any of the embodiments wherein the device for crossing occlusion 12 is power-assisted, impedance monitor 34 may further include a shut-off switch 34s such that when the impedance reaches a predetermined low limit, power to the device is shut-off. For example, power to atherectomy device 36 may be shut-off by switch 34s such that cutting head 38 stops rotating, thereby preventing cutting head 38 from damaging vessel 10.

Figure 8:
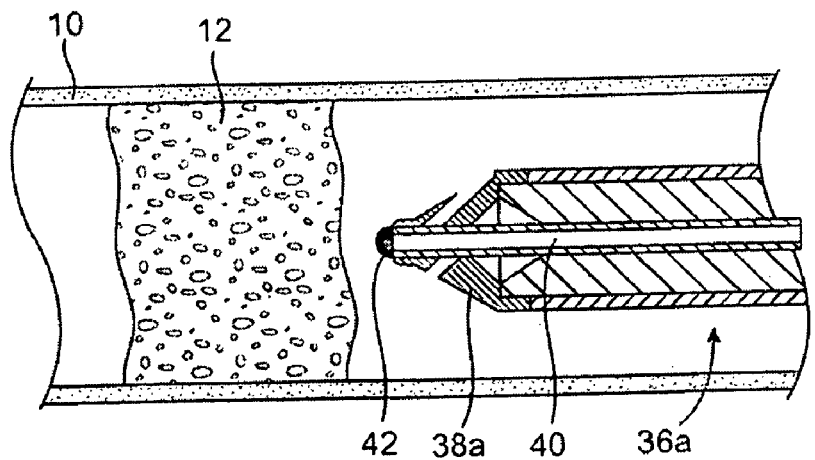
FIG. 8 is a cross-section of a vessel including an occlusion and showing another embodiment in accordance with the present disclosure.

FIG. 8 is an alternative embodiment of atherectomy device 36 shown in FIG. 7. An atherectomy device 36a of FIG. 8 includes a guidewire 40 disposed through and extending slightly beyond a cutting head 38a. A first electrode 42 is disposed at the distal tip of guidewire 40. Atherectomy device 36a functions in the same manner as the device of FIG. 7, except that the electrode is disposed in a different position.

Figure 9:
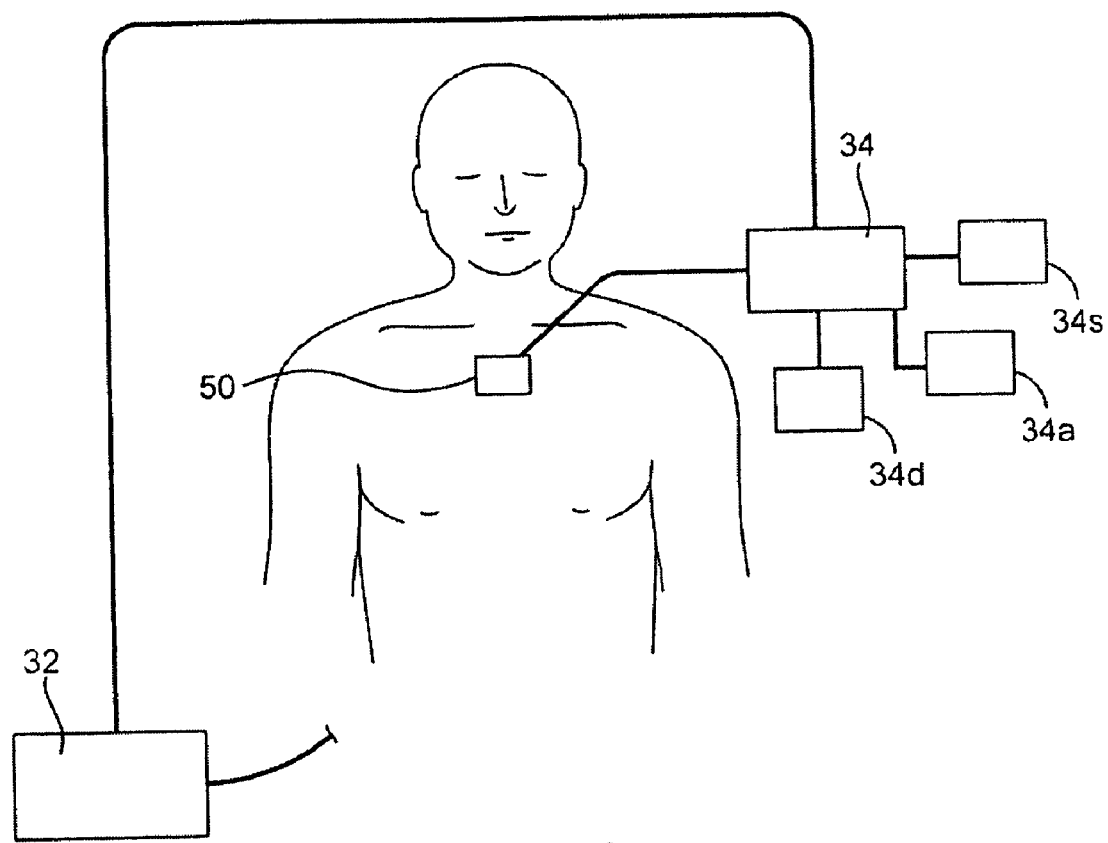
FIG. 9 is a plan view of a patient illustrating another embodiment in accordance with the present disclosure.

In an alternative to the embodiments described with respect to FIGS. 1-8, balloon 16 with ring electrode 18 is not required. Instead, a second, skin electrode 50 may be placed externally on the patient's chest, as shown in FIG. 9. In this embodiment, if one of first electrodes 26, 42 or 44 is in occlusion 12, not near the wall of vessel 10, then the impedance between first electrodes 26, 42 or 44 and skin electrode 50 may be safely above the bioelectric impedance threshold low limit and the clinician can continue advancing guidewire 22, atherectomy device 36, 36a, or a device for performing laser ablation, discectomy, or other similar procedures. When guidewire 22, atherectomy device 36, 36a, or a device for performing laser ablation, discectomy, or other similar procedures approaches the wall of vessel 10, the impedance between first electrodes 26, 42 or 44 and skin electrode 50 may approach the bioelectric impedance threshold low limit, and optionally providing an audible or visual signal to the clinician. When a signal is detected, the clinician may be alerted, for example, by impedance monitor 34, to indicate that the device crossing occlusion 12 may need to be redirected away from the wall of vessel 10. Upon examination, the clinician may determine that the device has safely passed through occlusion 12 and electrode 26, 42, or 44 may have contacted the wall of vessel 10 distal to occlusion 12.

Impedance monitor 34 may include display device 34d, alarm 34a, and shut-off switch 34s, as described with respect to the embodiment shown in FIG. 5. While the embodiment with skin electrode 50 is described in conjunction with the detection of any bioelectric impedance value indicating to the clinician that the device may be approaching the vessel wall, the embodiments may be interchangeable. For example, when using ring electrode 18 on balloon 16, a low value of impedance may not be detected between electrode 26, 42, or 44 and ring electrode 18 when guidewire 22 is near the center of occlusion 12. Factors such as the frequency of the current provided by power source 32 and the location of ring electrode 18, for example, may be adjusted so that the device functions in the "go/no-go" manner. Similarly, skin electrode 50 may be used in the embodiments described in FIGS. 1-8 such that changes in the measured bioelectric impedance may apprise the clinician of the anatomical location of the device in the patient, instead of providing information regarding the distance of the device from a surrounding vessel wall.

While various embodiments of the present disclosure have been described above, it should be understood that they have been presented by way of illustration and example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

The invention claimed is:

1. A method for guiding a device through an occlusion in a patient's vessel, the method comprising the steps of:
  delivering a flexible elongate steerable medical guidewire transluminally to the occlusion, wherein a first electrode is disposed on a distal tip of the guidewire;
  advancing the guidewire distal tip into the occlusion;
  placing on the patient a second electrode separate from the first electrode and in electrical contact with the patient, wherein the second electrode is a skin electrode;
  coupling an electric power source to the first and second electrodes;
  activating the power source to provide an electric current between the first and second electrodes;
  measuring a voltage drop between the first and second electrodes;
  calculating a bioelectric impedance based on the measured voltage drop between the first and second electrodes; and
  continuing to advance the guidewire distal tip through the occlusion while directing the guidewire tip away from the vessel wall when the calculated impedance reaches a predetermined bioelectric impedance value.

2. The method of claim 1, wherein the step of activating the power source to provide a current between the first and second electrodes takes place in a pulsed sequence.

3. The method of claim 2, wherein the impedance is calculated each time a current is provided between the first and second electrodes.

4. The method of claim 1, further comprising the step of advancing the guidewire through the occlusion as the current is applied between the first and second electrodes.

5. The method of claim 1, further comprising, prior to advancing the distal tip into the occlusion, the steps of:
  positioning the first electrode in electrical contact with the vessel adjacent the occlusion;
  measuring a voltage drop between the first electrode and the second electrode; and
  calculating the predetermined bioelectric impedance value based on the voltage drop between the first second electrodes.

6. The method of claim 1, wherein an alarm is triggered when the calculated impedance reaches a predetermined bioelectric impedance value.

* * * * *

UNITED STATES PATENT AND TRADEMARK OFFICE
CERTIFICATE OF CORRECTION

Page 1 of 1

PATENT NO. : 7,854,740 B2
APPLICATION NO. : 12/417363
DATED : December 21, 2010
INVENTOR(S) : Alan Oliver Carney It is certified that error appears in the above-identified patent and that said Letters Patent is hereby corrected as shown below:

Cover page of Issued patent, item (75) "Alan Carney" should be changed to --Alan Oliver Carney--

Signed and Sealed this
Twenty-second Day of November, 2011

David J. Kappos
*Director of the United States Patent and Trademark Office*